(12) United States Patent
Hamroll et al.

(10) Patent No.: US 6,475,954 B2
(45) Date of Patent: Nov. 5, 2002

(54) SOLID GLYPHOSPHATE-FORMULATION AND MANUFACTURING PROCESS

(75) Inventors: Bernd Hamroll, Magdeburg (DE);
Günter Dittrich, Magdeburg (DE);
Bernd Müller, Magdeburg (DE)

(73) Assignee: Schirm AG, Dortmund (DE)

( * ) Notice: Subject to any disclaimer, the term of this patent is extended or adjusted under 35 U.S.C. 154(b) by 0 days.

(21) Appl. No.: 09/969,168

(22) Filed: Oct. 2, 2001

(65) Prior Publication Data

US 2002/0049140 A1 Apr. 25, 2002

(30) Foreign Application Priority Data

Oct. 23, 2000 (DE) .......................................... 100 52 489

(51) Int. Cl.⁷ .............................................. A01N 57/00
(52) U.S. Cl. ...................................... 504/206; 504/127
(58) Field of Search .......................................... 504/206

(56) References Cited

U.S. PATENT DOCUMENTS 3,799,758 A    3/1974   Franz ............................ 71/86
4,140,513 A    2/1979   Prill ............................. 71/86

FOREIGN PATENT DOCUMENTS

| EP | 0498145 | 8/1982 |
|----|---------|--------|
| EP | 0220902 | 5/1987 |
| EP | 0255760 | 2/1988 |
| EP | 0378985 | 7/1990 |
| EP | 0448538 | 9/1991 |
| WO | WO 93/25081 | 12/1993 |

*Primary Examiner*—Alton Pryor
(74) *Attorney, Agent, or Firm*—Cohen, Pontani, Lieberman & Pavane

(57) ABSTRACT

Disclosed is a solid formulation of the herbicidal active agent glyphosate [N-(phosphonomethyl)glycine] compressed into tablet form. It is applied in the agricultural and horticultural sectors to destroy unwanted vegetation. The solid formulation according to the invention consists essentially of free glyphosate acid, salifying agents (alkali or ammonium hydrogencarbonate or carbonate in conjunction with solid organic acids), biological activating agents and diluents. A suitably sized tablet can consequently be adapted to supply an appropriate dose of spray mixture per surface unit for small-scale users. Submerging in water causes the glyphosate to convert into a soluble salt. The resulting carbon dioxide facilitates rapid disintegration of the tablet.

18 Claims, No Drawings

SOLID GLYPHOSATE-FORMULATION AND MANUFACTURING PROCESS

BACKGROUND OF THE INVENTION

The invention is in a composition of a solid, hydrosoluble formulation containing glyphosate as the active agent for the destruction and/or control of unwanted vegetation and a process for the manufacture of the composition.

Glyphosate [N-phosphonomethyl)glycine] is generally recognized as a highly-effective and efficient herbicide. It is also known that glyphosate is an organic acid which is relatively insoluble in water. Consequently, glyphosate acid is applied as a hydrosoluble salt.

The formulation and application of glyphosate as an ammonium or isopropyl ammonium salt is widespread (U.S. Pat. No. 3,799,758 and Proc. North Cent. Weed Control Conf., 1971, 26, 64).

The manufacture and application of a hydrosoluble glyphosate formulation containing sodium salt has also been the subject of many publications (e.g. U.S. Pat. No. 4,140,513).

Auxiliary agents and/or components to improve effectiveness have also been added to solid glyphosate salt formulations in the prior art. Commonly used additives are ionic and non-ionic surfactants, biological activating agents, extenders, bonding agents and diluents, anticaking agents, foam inhibitors and thickeners (ER 220902, EP 255760, EP 378985, EP 498145, EP 448538, WO 93/25081, Monsanto Research Disclosure No. 27161 "Novel Glyphosate acid wetcake powder formulation effective in control of weeds").

Commercial liquid glyphosate formulations can easily be diluted in water to the required concentration for application. Their disadvantage is their poor transportability, since these formulations contain more than 50% water.

The alternative is a solid, hydrosoluble formulation in the form of granules, pellets, pastes or spray dried powders. The disadvantage with these solid formulations is the high cost of manufacture since they generally originate as a glyphosate wetcake or slurry which must then, after homogenization of the components, be desiccated at high energy costs.

A further disadvantage for the small-scale user is that he must weigh out partial quantities to treat small areas. This can easily result in dosage errors, with either too much or too little being applied.

The objectives of the present invention are to avoid the aforementioned disadvantages for the small-scale user, to provide a composition for a solid glyphosate salt formulation which is easy to dose, dissolves quickly in water, is inexpensive and is therefore consumer-friendly, as well as a process for its manufacture.

THE INVENTION

The objectives are obtained by a composition of the invention. The invention accordingly comprises a solid, hydrosoluble composition for horticultural and agricultural use in the destruction and/or control of unwanted vegetation with the herbicidal active agent glyphosate in the form of its salts, containing the following minimum components:

10 to 30 wt.-% of N-(phosphonomethyl)glycine (glyphosate);
12 to 52 wt.-% of alkali or ammonium hydrogencarbonate or carbonate;
10 to 20 wt.-% of citric acid, oxalic acid or adipic acid;
0.5 to 2 wt.-% of hydrosoluble cellulose;
8 to 12 wt.-% of alkyl ether sulphosuccinates, alkyl ether phosphates; ethoxylated fatty amines and/or ethoxylated fatty alcohols;
50 to 60 wt.-% of alkali or ammonium hydrogencarbonate or carbonate; ammonium sulphate, urea;
0.2 to 1 wt.-% of polydimethyl siloxane; and
1 to 5 wt.-% of polyether siloxane.

In a preferred embodiment the composition has a glyphosate content of 18 to 22 wt.-% and about 10 wt.-% of a surfactant of one or more of ether sulphosuccinate, alkyl ether phosphate, ethoxylated fatty amine and/or ethoxylated fatty alcohol.

Sodium, potassium and/or ammonium are used as salt-forming cations.

Alkyl ether sulphosuccinates, alkyl ether phosphates, ethoxylated fatty alcohols and/or ethoxylated fatty amines are used as surfactants. Apart from their surface-active effect, the surfactants used also serve to reinforce the herbicidal effect (biological activating agents). Polyether siloxanes are also used as biological activating agents. Alkali and/or ammonium hydrogencarbonates or carbonates are used in conjunction with the organic acids such as citric acid, oxalic acid or adipic acid and hydrosoluble cellulose to accelerate disintegration, producing carbon dioxide bubbles, while sodium, potassium and/or ammonium hydrogencarbonate or carbonate, urea and alkali and/or ammonium sulphate are used as extenders, bonding agents and/or diluents. Polydimethyl siloxanes are used as foam inhibitors.

It has been discovered that the homogenized components of the formulation could be compressed into stable tablets, and that these tablets effervesced and dissolved clearly in water. The dose and size of the tablet can be adapted to contain the required defined quantity of glyphosate active agent for 5, 10 or 20 litres of spray mixture.

The formulation of this solid material is manufactured in accordance with a particularly preferred feature of the invention by homogenizing components of the formulation and compressing them into an effervescent tablet in a suitable tablet press. A tablet press such as the Korsch EK 4, for instance. would be suitable for weights of 2 to 35 g. The tablet mixture is compressed at a pressure of 70 to 80 newtons. The resulting tablet (e.g. for 10 litres spray mixture) has a weight of 6 to 7 g, a diameter of about 30 mm and a depth of about 6 to 8 mm.

EXAMPLES

There follows a list of 16 recipes for the formulation which can be homogenized and manufactured in tablet form by the process described above:

Example 1

21% glyphosate free acid (95%)
12% sodium hydrogencarbonate
10% Geropon CF/320
57% ammonium sulphate

Example 2

21% glyphosate free acid (95%)
14% sodium carbonate
10% Geropon CF/320
55% ammonium sulphate

Example 3

21% glyphosate free acid (95%)
13% potassium hydrogencarbonate

10% Geropon CF/320
56% ammonium sulphate

Example 4

21% glyphosate free acid (95%)
17% potassium carbonate
10% Geropon CF/320
52% ammonium sulphate

Example 5

21% glyphosate free acid (95%)
12% sodium hydrogencarbonate
10% Geropon CF/320
56% urea
1% hydrosoluble cellulose

Example 6

21% glyphosate free acid (95%)
11% ammonium hydrogencarbonate
10% Geropon CF/320
58% ammonium sulphate

Example 7

21% glyphosate free acid (95%)
11% ammonium hydrogencarbonate
10% Geronol CFAR
58% ammonium sulphate

Example 8

21% glyphosate free acid (95%)
11% ammonium hydrogencarbonate
10% Rhodameen CF/15H
58% ammonium sulphate

Example 9

21% glyphosate free acid (95%)
11% ammonium hydrogencarbonate
10% Rhodasurf D/202
58% ammonium sulphate

Example 10

21% glyphosate free acid (95%)
11% ammonium hydrogencarbonate
10% Geropon CF/320
58% sodium sulphate

Example 11

21% glyphosate free acid (95%)
52% sodium hydrogencarbonate
10% Geropon CF/320
17% citric acid monohydrate

Example 12

21% glyphosate free acid (95%)
54% sodium hydrogencarbonate
10% Geropon CF1320
15% oxalic acid dihydrate

Example 13

21% glyphosate free acid (95%)
53% sodium hydrogencarbonate
10% Geropon CF/320
16% adipic acid

Example 14

21% glyphosate free acid (95%)
51.6% ammonium hydrogencarbonate
10% Geropon CF/320
17.4% citric acid monohydrate

Example 15

21% glyphosate free acid (95%)
52% sodium hydrogencarbonate
9.7% Geropon CF/320
17% citric acid monohydrate
0.3% Rhodorsil Antifoam 6703

Example 16

21% glyphosate free acid (95%)
52% sodium hydrogencarbonate
8% Geropon CF/320
2% Break-Thru S 275 DS
17% citric acid monohydrate The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A solid hydrosoluble composition comprising:
   a) 10 to 30 wt.-% of N-(phosphonomethyl)glycine (glyphosate);
   b) 12 to 52 wt.-% of a salt forming agent;
   c) 10 to 20 wt.-% of citric acid, oxalic acid or adipic acid;
   d) 0.5 to 2 wt.-% of hydrosoluble cellulose;
   e) 8 to 12 wt.-% of alkyl ether sulphosuccinate, alkyl ether phosphate, ethoxylated fatty amine and/or an ethoxylated fatty alcohol;
   f) 50 to 60 wt.-% of a bonding agent;
   g) 0.2 to 1 wt.-% of polydimethyl siloxane; and
   h) 1 to 5 wt.-% of polyether siloxane.

2. The composition of claim 1 comprising 18 to 22 wt.-% N-(phosphonomethyl)glycine (glyphosate) content.

3. The composition of claim 1 comprising 10 wt.-% of at least one of alkyl ether sulphosuccinate, alkyl ether phosphate, and ethoxylated fatty amine and/or ethoxylated fatty alcohol.

4. The composition of claim 1 in tablet form.

5. The composition of claim 4 wherein the tablet form is effervescent in water to produce a clear solution.

6. A tablet comprising the composition of claim 1 wherein the tablet comprises an amount of active agent glyphosate for 5, 10 or 20 litres of spray mixture.

7. A process to manufacture a composition comprising: mixing and homogenizing the composition of claim 1 to form a mixture; and compressing the mixture into a tablet at a pressure of 70 to 80 newtons.

8. The process of claim 7 wherein the composition comprises 18 to 22 wt.-% N(phosphonomethyl)glycine (glyphosate) content.

9. The process of claim 7 wherein the composition comprises 10 wt.-% of at least one of alkyl ether sulphosuccinate, alkyl ether phosphate, and ethoxylated fatty amine and/or ethoxylated fatty alcohol.

10. The composition of claim 1 wherein the salt forming agent is at least one compound selected from alkali hydrogencarbonate and alkali carbonate and the bonding agent is at least one component selected from ammonium hydrogencarbonate, ammonium carbonate, ammonium sulphate and urea.

11. The composition of claim 1 wherein the salt forming agent is at least one compound selected from sodium hydrogencarbonate and sodium carbonate and the bonding agent is at least one component selected from ammonium hydrogencarbonate, ammonium carbonate, ammonium sulphate and urea.

12. The composition of claim 1 wherein the salt forming agent is potassium hydrogencarbonate and the bonding agent is at least one component selected from ammonium hydrogencarbonate, ammonium carbonate, ammonium sulphate and urea.

13. The composition of claim 1 wherein the salt forming agent is potassium carbonate and the bonding agent is at least one component selected from ammonium hydrogencarbonate or carbonate, ammonium sulphate and urea.

14. The composition of claim 1 wherein the salt forming agent is ammonium hydrogencarbonate and the bonding agent is at least one compound selected from alkali carbonate, ammonium carbonate, ammonium sulphate and urea.

15. The composition of claim 1 wherein the salt forming agent is at least one compound selected from alkali hydrogencarbonate, ammonium hydrogencarbonate, alkali carbonate, and ammonium carbonate and the bonding agent is at least one compound selected from ammonium sulphate and urea.

16. The composition of claim 1 wherein the salt forming agent is at least one compound selected from alkali hydrogen carbonate and alkali carbonate and the bonding agent is at least one compound selected from ammonium hydrogen carbonate, ammonium carbonate, ammonium sulphate and urea.

17. The composition of claim 1 wherein the salt forming agent is at least one compound selected from ammonium hydrogen carbonate and ammonium carbonate and the bonding agent is at least one compound selected from alkali hydrogencarbonate or carbonate, ammonium sulphate and urea.

18. A composition comprising: an aqueous solution of
a) 10 to 30 wt.-% of N-(phosphonomethyl)glycine (glyphosate);
b) 12 to 52 wt.-% of a salt forming agent;
c) 10 to 20 wt.-% of citric acid, oxalic acid or adipic acid;
d) 0.5 to 2 wt.-% of hydrosoluble cellulose;
e) 8 to 12 wt.-% of alkyl ether sulphosuccinate, alkyl ether phosphate, ethoxylated fatty amine and/or an ethoxylated fatty alcohol;
f) 50 to 60 wt.-% of a bonding agent;
g) 0.2 to 1 wt.-% of polydimethyl siloxane; and
h) 1 to 5 wt.-% of polyether siloxane.

* * * * *